(12) United States Patent
Steiner et al.

(10) Patent No.: US 6,355,647 B1
(45) Date of Patent: Mar. 12, 2002

(54) 3-SUBSTITUTED 3,4,5,7-TETRAHEDROPYRROLO[3',4':4,5]THIENO-[2,3-D]PYRIMIDINE DERIVATIVES, THEIR PREPARATION AND USE

(75) Inventors: Gerd Steiner, Kirchheim; Uta Dullweber, Frankenthal; Dorothea Starck, Ludwigshafen; Alfred Bach, Heidelberg; Karsten Wicke, Altrip; Hans-Jürgen Teschendorf, Dudenhofen; Francisco-Javier Garcia-Ladona, Kandel; Franz Emling, Ludwigshafen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/485,188

(22) PCT Filed: Jul. 23, 1998

(86) PCT No.: PCT/EP98/04633

§ 371 Date: Feb. 7, 2000

§ 102(e) Date: Feb. 7, 2000

(87) PCT Pub. No.: WO99/07711

PCT Pub. Date: Feb. 18, 1999

(30) Foreign Application Priority Data

Aug. 8, 1997 (DE) .......................... 197 34 444

(51) Int. Cl.⁷ ..................... C07D 495/14; A61K 31/435
(52) U.S. Cl. ....................... 514/267; 544/250
(58) Field of Search .................. 544/250; 514/267

(56) References Cited

U.S. PATENT DOCUMENTS 4,835,157 A    5/1989   Press et al. ............... 514/258

FOREIGN PATENT DOCUMENTS

EP    329 168    8/1989
WO    98/11110   3/1998

OTHER PUBLICATIONS

Fink et al., Arch. Pharm. 1995, 352:451–454.
Behavioural Brain Res. 73 (1996) 79–82, Price et al.
Neuropharm. vol.34, No. 4, 383–392, 1995, Hutson et al.
Neuropharm. vol.34, No. 4, 377–382,1995, Skingle et al.
Neurosci. Ltrs 188(1995)41–44,Daidson et al.
Neuropharm. vol.33, No.3/4,393–402,1994, Starkey et al.

*Primary Examiner*—Mukund J. Shah
*Assistant Examiner*—Hong Liu
(74) *Attorney, Agent, or Firm*—Keil & Weinakuf

(57) ABSTRACT

3-Substituted 3,4,5,7-tetrahydropyrrolo[3',4':4,5]thieno-[2,3-d]pyrimidine derivatives of the formula I

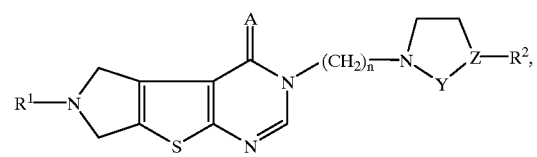

in which the substituents have the meanings stated in the description, their preparation and their use as drugs.

13 Claims, No Drawings

3-SUBSTITUTED 3,4,5,7-TETRAHEDROPYRROLO[3',4':4,5] THIENO[2,3-D]PYRIMIDINE DERIVATIVES, THEIR PREPARATION AND USE

The invention relates to novel 3-substituted 3,4,5,7-tetrahydropyrrolo[3',4':4,5]thieno[2,3-d]pyrimidine derivatives, their preparation and use for preparing active ingredients of drugs.

Classical antidepressants, and the newer selective serotonin reuptake inhibitors (SSRIs), exert their antidepressant effect inter alia by inhibiting active reuptake of the transmitter into the presynaptic nerve endings. Unfortunately, in this case the antidepressant effect has its onset only after treatment for at least 3 weeks and, moreover, about 30% of patients are therapy-resistant.

Blockade of presynaptic serotonin autoreceptors increases, by abolishing negative coupling, the serotonin release and thus the instantaneous transmitter concentration in the synaptic cleft. This increase in the transmitter concentration is regarded as the principle of the antidepressant effect. This mechanism of action differs from that of previously disclosed antidepressants which activate both the presynaptic and somatodendritic autoreceptors and therefore result in the delayed onset of action only after desensitization of these autoreceptors. Direct autoreceptor blockade bypasses this effect.

According to current knowledge, the presynaptic serotonin autoreceptor is of the 5-HT$_{1B}$ subtype (Fink et al., Arch. Pharmacol. 352 (1995), 451). Selective blockade thereof by 5-HT$_{1B/D}$ antagonists increases serotonin release in the brain: G. W. Price et al., Behavioural Brain Research 73 (1996), 79–82; P. H. Hutson et al., Neuropharmacology Vol. 34, No. 4 (1995), 383–392.

However, surprisingly, the selective 5-HT$_{1B}$ antagonist GR 127 935 reduces serotonin release in the cortex after systemic administration. One explanation might be stimulation of somatodendritic 5-HT$_{1A}$ receptors in the raphe region by the released serotonin, which inhibits the rate of firing of serotonergic neurones and thus serotonin secretion (M. Skingle et al., Neuropharmacology Vol. 34 No. 4 (1995), 377–382, 393–402).

One strategy for bypassing the autoinhibitory effects in serotonergic areas of origin thus aims at blockade of the presynaptic 5-HT$_{1B}$ receptors. This hypothesis is supported by the observation that the effect of paroxetine on serotonin release in the dorsal raphe nucleus of the rat is potentiated by the 5-HT$_{1B}$ receptor antagonist GR 127 935 (Davidson and Stamford, Neuroscience Letts., 188 (1995),41).

The second strategy includes blockade of both types of autoreceptors, namely the 5-HT$_{1A}$ receptors, in order to enhance neuronal firing, and the 5-HT$_{1B}$ receptors, in order to increase terminal serotonin release (Starkey and Skingle, Neuropharmacology 33 (3–4) (1994),393).

5-HT$_{1B/D}$ antagonists, alone or coupled with a 5-HT$_{1A}$ receptor antagonistic component, ought therefore to cause a greater increase in serotonin release in the brain and might therefore entail advantages in the therapy of depression and related psychological disorders.

It has now been found that 3-substituted 3,4,5,7-tetrahydropyrrolo[3',4':4,5]thieno[2,3-d]pyrimidine derivatives of the formula I

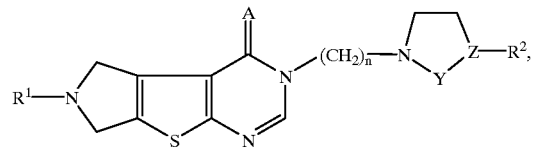

where
R$^1$ is a hydrogen atom, a C$_1$–C$_4$-alkyl group, an acetyl group, a phenylalkyl C$_1$–C$_4$ radical where the aromatic ring is unsubstituted or substituted by halogen, C$_1$–C$_4$-alkyl, trifluoromethyl, hydroxyl, C$_1$–C$_4$-alkoxy, amino, cyano or nitro groups, or is a C$_1$–C$_3$-alkyl carboxylate radical, R$^2$ is a phenyl, pyridyl, pyrimidinyl or pyrazinyl group which is unsubstituted or mono- or disubstituted by halogen atoms, C$_1$–C$_4$-alkyl, trifluoromethyl, trifluoromethoxy, hydroxyl, C$_1$–C$_4$-alkoxy, amino, monomethylamino, dimethylamino, cyano or nitro groups, and may be fused to a benzene nucleus which may be mono- or disubstituted by halogen atoms, C$_1$–C$_4$-alkyl, hydroxyl, trifluoromethyl, C$_1$–C$_4$-alkoxy, amino, cyano or nitro groups and may contain 1 nitrogen atom, or to a 5- or 6-membered ring which may contain 1–2 oxygen atoms, A is NH or an oxygen atom, Y is CH$_2$, CH$_2$—CH$_2$, CH$_2$—CH$_2$—CH$_2$ or CH$_2$—CH Z is a nitrogen atom, carbon atom or CH, where the linkage between Y and Z may also be a double bond, and n is 2, 3 or 4, or a physiologically tolerated salt thereof, have valuable pharmacological properties.

Particularly preferred compounds are those where
R$^1$ is hydrogen, ethyl, ethyl carboxylate
R$^2$ is o-methoxyphenyl, 1-naphthyl, 2-methoxy-1-naphthyl, 2-methyl-1-naphthyl
A is an oxygen atom
y is CH$_2$—CH$_2$
Z is a nitrogen atom
and n is 2 and 3.

The novel compounds of the formula I can be prepared by reacting a compound of the formula II

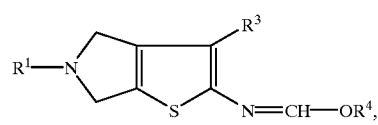

where R$^1$ has the abovementioned meaning, R$^3$ is a cyano group or a C$_{1-3}$-alkyl carboxylate group, and R$^4$ is C$_{1-3}$-alkyl, with a primary amine of the formula III

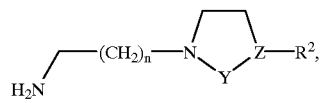

where R$^2$ has the abovementioned meaning, and converting the compound obtained in this way where appropriate into the addition salt with a physiologically tolerated acid.

The reaction is expediently carried out in an inert organic solvent, in particular a lower alcohol, eg. methanol or ethanol, or a saturated cyclic ether, in particular tetrahydrofuran or dioxane.

The reaction is, as a rule, carried out at from 20 to 110° C., in particularly from 60 to 90° C., and is generally complete within 1 to 10 hours.

Or a compound of the formula II

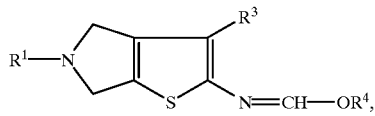

where $R^1$ has the abovementioned meaning, $R^3$ is a cyano group or a $C_{1-3}$-alkyl carboxylate group, and $R^4$ is $C_{1-3}$-alkyl, is reacted with a primary amino alcohol of the formula IV

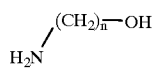

in an inert solvent, preferably alcohols such as ethanol, at from 60° to 120° C. to give the cyclization product V (X=OH)

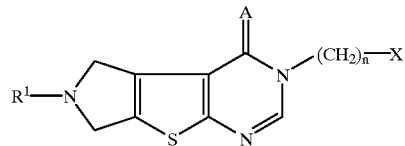

which is subsequently converted with a halogenating agent, eg. thionyl chloride or hydrobromic acid, in an organic solvent such as a halohydrocarbon or without solvent, at from room temperature to 100° C., into the corresponding halogen derivative V (X=Cl, Br). Finally, the halogen derivative of the formula V (X=Cl, Br) is reacted with an amine of the formula VI

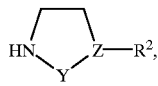

where Y, Z and $R^2$ have the abovementioned meanings, to give the novel final product of the formula I. This reaction takes place best in an inert organic solvent, preferably toluene or xylene, in the presence of a base, eg. potassium carbonate or potassium hydroxide, at from 60° C. to 150° C.

The novel compounds of the formula I can be either recrystallized by recrystallization from conventional organic solvents, preferably from a lower alcohol such as ethanol, or purified by column chromatography.

The free 3-substituted 3,4,5,7-tetrahydropyrrolo[3',4':4,5]-thieno[2,3-d]pyrimidine derivatives of the formula I are converted in a conventional way into the acid addition salts with a solution containing the stoichiometric amount of the appropriate acid. Examples of pharmaceutically acceptable acids are hydrochloric acid, phosphoric acid, sulfuric acid, methanesulfonic acid, sulfamic acid, maleic acid, fumaric acid, oxalic acid, tartaric acid or citric acid.

The invention also accordingly relates to a therapeutic composition which comprises a compound of the formula I or its pharmacologically acceptable acid addition salt as active ingredient in addition to conventional excipients and diluents, and to the use of the novel compounds for controlling diseases.

The novel compounds can be administered in a conventional way orally or parenterally, intravenously or intramuscularly.

The dosage depends on the age, condition and weight of the patient and on the mode of administration. The daily dose of active ingredient is, as a rule, from about 1 to 100 mg/kg of body weight on oral administration and from 0.1 to 10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional way. The active ingredients can for this purpose be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain from 1 to 99% by weight of active ingredient.

The substances of the formula II to VI required as starting materials for synthesizing the novel compounds are known or can be synthesized by preparation methods described in the literature from appropriate starting materials (F. Sauter and P. Stanetty, Monatsh. Chem. 106(5) (1975) 1111–1116; K. Gewald et al., Chem. Ber. 9 (1966) 94–100, DE Patent Application 196 36769.7).

The novel compounds have a high affinity for the 5-HT$_{1B}$, 5-HT$_{1D}$ and 5-HT$_{1A}$ serotonin receptors. The affinity for these receptors is moreover approximately the same, at least of the same order of magnitude. Furthermore, some of the novel compounds show good serotonin reuptake inhibition, which is a principle implemented with most antidepressants.

These compounds are suitable as drugs for treating pathological states in which the serotonin concentration is reduced and in which it is wished as part of a treatment to block specifically the activity of the 5-HT$_{1B}$, 5-HT$_{1A}$ and 5-HT$_{1D}$ presynaptic receptors without greatly affecting other receptors at the same time. An example of a pathological state of this type is depression.

The compounds of the present invention may also be beneficial for treating mood disturbances with a central nervous causation, such as seasonal affective disorders and dysthymia. These also include anxiety states such as generalized anxiety, panic attacks, sociophobia, obsessive-compulsive neuroses and post-traumatic stress symptoms, memory disturbances including dementia, amnesias and age-related memory loss, and psychogenic eating disorders such as anorexia nervosa and bulimia nervosa.

The novel compounds may additionally be beneficial for treating endocrine disorders such as hyperprolactinemia and for treating asospasms (especially of the cerebral vessels), hypertension and gastrointestinal disorders associated with motility and secretion disturbances. Another area of use comprises sexual disorders.

The following examples serve to illustrate the invention:

A Preparation of Starting Materials a) 2-Amino-3,5-dicarbethoxy-4,6-dihydrothieno[3,2-c]pyrrole 16.1 ml (150 mM) of ethyl cyanoacetate and 4.8 g (150 mM) of sulfur powder were added to 23.6 g (150 mM) of ethyl 3-pyrrolidinone-1-carboxylate (Kuhn, Osswald: Chem. Ber. 89, 1435 (1956)) in 60 ml of ethanol and then, while stirring efficiently and under a nitrogen atmosphere, 15.6 ml (112 mM) of triethylamine were added dropwise. The mixture was then left to stir at room temperature overnight. The residue after concentration of the mixture was dissolved in 70 ml of ethyl acetate and left to crystallize with stirring. After cooling, the crystals were filtered off with suction and washed with a little cold ethyl acetate. 13.2 g (31%) of product with melting point 154–156° C. were isolated.

b) 2-Ethoxymethyleneamino-3,5-dicarbethoxy-4,6-dihydrothieno-[3,2-c]pyrrole 0.3 ml of acetic anhydride was added to 1.4 g (4.8 mM) of 2-amino-3,5-dicarbethoxy-4,6-dihydrothieno[3,2-c]pyrrole in 14 ml of triethylorthoformate and refluxed under nitrogen for 1 h. The mixture was then completely evaporated in a rotary evaporator at 80° C. 1.6 g (99%) of crude product were isolated as a viscous oil which is sufficiently pure for further reactions.

c) 3-(2-Hydroxyethyl)-6-carbethoxy-3,4,5,7-tetrahydropyrrolo[3',4':4,5]thieno[2,3-d]pyrimidin-4-one 13 ml (215 mM) of ethanolamine were added to 15.5 g (46 mM) of 2-ethoxymethyleneamino-3-carboethoxy-5-ethyl-4,5,6,7-tetrahydrothieno[3,2-c]pyridine in 250 ml of ethanol and refluxed for 3 h. The mixture was then allowed to cool and was stirred in an ice bath. The precipitated fine solid was filtered off with suction and washed with cold ethyl acetate. 5.5 g (36%) of pale brown product were isolated. Melting point 243–245° C.

d) 3-(2-Chloroethyl)-6-carbethoxy-3,4,5,7-tetrahydropyrrolo-[3',4':4,5]thieno[2,3-d]pyrimidin-4-one 5.5 g (17.8 mM) of 3-(2-hydroxyethyl)-6-ethyl-3,4,5,6,7,8-hexahydropyrido[3',4':4,5]thieno[2,3-d]pyrimidin-4-one in 50 ml of 1,2-dichloroethane were heated to reflux (slow dissolution) and then 2 ml (27 mM) of thionyl chloride in 10 ml of 1,2-dichloroethane were added dropwise. The mixture was refluxed for 1 h and then concentrated and stirred in a little dichloromethane, and the solid was filtered off with suction. 5.4 g (92%) of product were isolated and were sufficiently pure for further reactions, melting point 169–171° C.

e) N-(1-Naphthyl)piperazine 83.2 g (966 mM) of piperazine, 38.0 g (339 mM) of potassium tert-butoxide and 50.0 g (241 mM) of 1-bromonaphthalene were added to a mixture of 5.4 g (24.2 mM) of palladium acetate and 14.7 g (48.3 mM) of tri-o-tolylphosphine in 500 ml of xylene, and the mixture was refluxed with efficient stirring under a nitrogen atmosphere for 10 h. The mixture was then diluted with methylene chloride, the insoluble residues were filtered off and the filtrate was concentrated. The crude product was purified by column chromatography (silica gel, mobile phase THF/methanol/ammonia 85/13/2). 21.5 g (42%) of product were isolated with melting point 84–86° C.

f) N-(2-Methyl-1-naphthyl)piperazine 14.7 g (82.7 mM) of bis(2-chloroethyl)amine×HCl were added to 13.0 g (82.7 mM) of 1-amino-2-methylnaphthalene in 100 ml of chlorobenzene and refluxed under nitrogen for 90 h. The mixture was then concentrated and partitioned between methylene chloride and water at pH=9, and the organic phase was dried and concentrated. The crude product was purified by column chromatography (silica gel, mobile phase/THF/methanol/ammonia 85/13/2. 11.6 g (62%) of product were isolated.

g) 4-Piperazin-1-ylisoquinoline 4.51 g (21.7 mM) of 4-bromoisoquinoline, 4.65 g (25.0 mM) of t-butyl piperazine-N-carboxylate, 0.1 g (0.11 mM) of tris(dibenzylideneacetone)dipalladium, 0.11 g (0.18 mM) of 2,2'-bis(diphenylphosphino)-1,1'-binaphthyl and 2.92 g (30.4 mM) of sodium t-butoxide were mixed in 50 ml of toluene and stirred at 75° C. for 2 h. The reaction mixture was added to ice/sodium chloride and extracted with ethyl acetate, the organic phase was dried over sodium sulfate, and the solvent was removed in a rotary evaporator. The product crystallized out and was filtered off with suction and washed with pentane. 5.5 g (81%) of the Boc-protected piperazine were obtained (melting point: 111° C.). 5.2 g (16.6 mM) of this substance were taken up in 17 ml of dichloromethane and, at 0° C., slowly taken up with 17 ml of dichloromethone and, at 0° C., 17 ml (0.22 mM) of trifluoroacetic acid were slowly added. The mixture was left to stir at 0° C. for 4 h, poured into ice-water and extracted with dichloromethane. The aqueous phase was filtered, made alkaline and extracted with dichloromethane. Drying over sodium sulfate and substantial remove of the solvent was followed by dilution with diethyl ether and precipitation of the hydrochloride with ethereal hydrochloric acid. 3.2 g (67%) of the product were obtained with melting point 293–294° C.

Further piperazine derivatives (see examples) not disclosed in the literature (cf. also DE Patent Application 19636769.7) were prepared as in e), f) and g).

B Preparation of the Final Products

EXAMPLE 1

3,4,5,7-Tetrahydro-6-carbethoxy-3-[2-(4-(2-methoxyphenyl)-1-piperazinyl)ethyl]pyrrolo[3',4':4,5]thieno[2,3-d]pyrimidin-4-one 1.1 g (4.8 mM) of 1-(2-aminoethyl)-4-(2-methoxyphenyl)-piperazine were added to 1.6 g (4.8 mM) of 2-ethoxymethyleneamino-3,5-dicarbethoxy-4,6-dihydrothieno[3,2-c]pyrrole in 25 ml of ethanol and refluxed for 2 h. The mixture was then concentrated in a rotary evaporator, and the crude product was purified by column chromatography (silica gel, mobile phase methylene chloride/methanol 96/4). After recrystallization from ethyl acetate, 1.1 g (47%) of product were isolated with melting point 153–155° C.

EXAMPLE 2

3,4,5,7-Tetrahydro-6-carbethoxy-3-[2-(4-naphth-1-ylhexahydro-1,4-diazepin-1-yl)ethyl]pyrrolo[3',4':4,5]thieno[2,3-d]pyrimidin-4-one 0.7 g (3.0 mM) of N-(2-methoxy-1-naphthyl)piperazine and 0.5 g (3.6 mM) of finely powdered potassium carbonate were added to 1.0 g (3.0 mM) of 3-(2-chloroethyl)-6-carbethoxy-3,4,5,7-tetrahydropyrrolo[3',4':4,5]thieno[2,3-d]pyrimidin-4-one in 40 ml and refluxed under nitrogen for a total of 70 h. The mixture was then concentrated under reduced pressure, and the residue was partitioned at pH=10 between methylene chloride and water. The organic phases were dried and concentrated, and then the crude product was purified by MPLC (mobile phase methanol/dichloromethane). 0.6 g (38%) of hydrochloride with melting point 160° C. (decomposition) was isolated by precipitation with ethereal hydrochloric acid from a solution of the product in acetone.

EXAMPLE 3

3,4,5,7-Tetrahydro-3-[2-(4-(1-naphthyl)-1-piperazinyl)ethyl]-pyrrolo[3',4':4,5]thieno[2,3-d]pyrimidin-4-one×2 HCl×2 H$_2$O 9.4 g (18.7 mM) of 3,4,5,7-tetrahydro-6-carbethoxy-3-[2-(4-(1-naphthyl)-1-piperazinyl)ethyl]pyrrolo[3',4':4,5]-thieno[2,3-d]pyrimidin-4-one were introduced into a mixture of 80 ml of conc. hydrochloric acid and 80 ml of water and then refluxed for 7 h. The reaction mixture was poured into ice-water, adjusted to pH=10 with conc. sodium hydroxide solution and extracted twice with methylene chloride. The organic phase was dried and concentrated and then the crude product was purified by column chromaatography (silica gel, mobile phase methylene chloride/methanol 90/10). 2.4 g (30%) of product were isolated and were dissolved in ethyl acetate and converted into the hydrochloride of melting point 288–290° C. (decomposition).

EXAMPLE 4

3,4,5,7-Tetrahydro-6-ethyl-3-[2-(4-(1-naphthyl)-1-piperazinyl)ethyl]pyrrolo[3',4':4,5]thieno[2,3-d]-pyrimidin-4-one×2 HCl×3 H$_2$O 0.68 ml (8.5 mM) of iodoethane and 0.5 g (3.5 mM) of finely powdered potassium carbonate were added to 1.5 g (3.5 mM) of 3,4,5,7-tetrahydro-3-[2-(4-(1-naphthyl)-1-piperazinyl)ethyl]pyrrolo[3',4':4,5]thieno[2,3-d]-pyrimidin-4-one in 30 ml of tetrahydrofuran and refluxed for 3 h. The mixture was then poured into ice/water, adjusted to pH=9 with ammonia and extracted twice with methylene chloride. The organic phase was dried and concentrated and then the crude product was purified by column chromatography (silica gel, mobile phase methylene chloride/methanol 95/5). 0.4 g (25%) of product was isolated and was dissolved in ethyl acetate and converted into the hydrochloride of melting point 202–204° C. (decomposition).

EXAMPLE 5

3,4,5,7-Tetrahydro-6-acetyl-3-[2-(4-(1-naphthyl)-1-piperazinyl)ethyl]pyrrolo[3',4':4,5]thieno[2,3-d]-pyrimidin-4-one

EXAMPLE 6

3,4,5,7-Tetrahydro-6-benzyl-3-[2-(4-(1-naphthyl)-1-piperazinyl)ethyl]pyrrolo[3',4':4,5]thieno[2,3-d]-pyrimidin-4-one

EXAMPLE 7

3,4,5,7-Tetrahydro-6-(4-chlorophenyl-2-ethyl)-3-[2-(4-(1-naphthyl)-1-piperazinyl)ethyl]pyrrolo[3',4':4,5]-thieno[2,3-d]-pyrimidin-4-one The following can be prepared as in Examples 1 to 7:
8. 3,4,5,7-Tetrahydro-6-carbethoxy-3-[2-(4-(1-naphthyl)-1-piperazinyl)ethyl]pyrrolo[3',4':4,5]thieno[2,3-d]-pyrimidin-4-one, melting point 190–192° C.
9. 3,4,5,7-Tetrahydro-6-carbethoxy-3-[2-(4-(2-methyl-1-naphthyl)-1-piperazinyl)ethyl]pyrrolo[3',4':4,5]-thieno[2,3-d]pyrimidin-4-one
10. 3,4,5,7-Tetrahydro-6-carbethoxy-3-[2-(4-(2-methoxy-1-naphthyl)-1-piperazinyl)ethyl]pyrrolo[3',4':4,5]-thieno[2,3-d]pyrimidin-4-one
11. 3,4,5,7-Tetrahydro-6-carbethoxy-3-[2-(4-pyrimidin-2-yl-1-piperazinyl)ethyl]pyrrolo[3',4':4,5]thieno[2,3-d]pyrimidin-4-one, melting point 166° C.
12. 3,4,5,7-Tetrahydro-6-carbethoxy-3-[2-(4-(2-methoxyphenyl)-1-piperidinyl)ethyl]pyrrolo[3',4':4,5]thieno[2,3-d]pyrimidin-4-one
13. 3,4,5,7-Tetrahydro-3-[2-(4-(2-methoxyphenyl)-1-piperazinyl)ethyl]pyrrolo[3',4':4,5]thieno[2,3-d]-pyrimidin-4-one
14. 3,4,5,7-Tetrahydro-3-[2-(4-naphth-1-ylhexahydro-1,4-diazepin-1-yl)ethyl]pyrrolo[3',4':4,5]thieno[2,3-d]pyrimidin-4-one
15. 3,4,5,7-Tetrahydro-3-[2-(4-(2-methylphenyl)-1-piperazinyl)ethyl]pyrrolo[3',4':4,5]thieno[2,3-d]pyrimidin-4-one
16. 3,4,5,7-Tetrahydro-3-[2-(4-tetralin-5-yl-1-piperazinyl)ethyl]pyrrolo[3',4':4,5]thieno[2,3-d]pyrimidin-4-one
17. 3,4,5,7-Tetrahydro-3-[2-(4-indan-1-yl-1-piperazinyl)ethyl]pyrrolo[3',4':4,5]thieno[2,3-d]pyrimidin-4-one
18. 3,4,5,7-Tetrahydro-3-[2-(4-(2-methoxyphenyl)-3,4-dehydro-1-piperidinyl)ethyl]pyrrolo[3',4':4,5]-thieno[2,3-d]pyrimidin-4-one
19. 3,4,5,7-Tetrahydro-3-[2-(4-naphth-1-yl-1-piperidinyl)-ethyl]pyrrolo[3',4':4,5]thieno[2,3-d]pyrimidin-4-one
20. 3,4,5,7-Tetrahydro-3-[2-(4-(2-methoxy-1-naphthyl-3,4-dehydro-1-piperidinyl)ethyl]pyrrolo-[3',4':4,5]thieno[2,3-d]-pyrimidin-4-one
21. 3,4,5,7-Tetrahydro-6-ethyl-3-[2-(4-(2-methoxyphenyl)-1-piperazinyl)ethyl]pyrrolo[3',4':4,5]thieno[2,3-d]pyrimidin-4-one
22. 3,4,5,7-Tetrahydro-6-ethyl-3-[2-(4-(2,3-dimethylphenyl)-1-piperazinyl)ethyl]pyrrolo[3',4':4,5]thieno[2,3-d]pyrimidin-4-one
23. 3,4,5,7-Tetrahydro-6-ethyl-3-[2-(4-(2-chlorophenyl)-1-piperazinyl)ethyl]pyrrolo[3',4':4,5]thieno[2,3-d]pyrimidin-4-one
24. 3,4,5,7-Tetrahydro-6-ethyl-3-[2-(4-pyrimidin-2-yl-1-piperazinyl)ethyl]pyrrolo[3',4':4,5]thieno[2,3-d]pyrimidin-4-one
25. 3,4,5,7-Tetrahydro-6-ethyl-3-[2-(4-pyridin-2-yl-1-piperazinyl)ethyl]pyrrolo[3',4':4,5]thieno[2,3-d]pyrimidin-4-one
26. 3,4,5,7-Tetrahydro-6-ethyl-3-[2-(4-quinolin-2-yl-1-piperazinyl)ethyl]pyrrolo[3',4':4,5]thieno[2,3-d]pyrimidin-4-one
27. 3,4,5,7-Tetrahydro-6-ethyl-3-[2-(4-(2-methoxyphenyl)-1-piperidinyl)ethyl]pyrrolo[3',4':4,5]thieno[2,3-d]pyrimidin-4-one
28. 3,4,5,7-Tetrahydro-6-ethyl-3-[3-(4-pyrimidin-2-yl-1-piperazinyl)propyl]pyrrolo[3',4':4,5]thieno[2,3-d]pyrimidin-4-one
29. 3,4,5,7-Tetrahydro-6-methyl-3-[2-(4-(3-trifluoromethylphenyl)-1-piperazinyl)ethyl]pyrrolo[3',4':4,5]thieno[2,3-d]pyrimidin-4-one
30. 3,4,5,7-Tetrahydro-6-methyl-3-[2-(4-(2-cyano-phenyl)-1-piperazinyl)ethyl]pyrrolo[3',4':4,5]thieno[2,3-d]pyrimidin-4-one
31. 3,4,5,7-Tetrahydro-6-methyl-3-[2-(4-isoquinolin-4-yl-1-piperazinyl)ethyl]pyrrolo[3',4':4,5]thieno[2,3-d]pyrimidin-4-one
32. 3,4,5,7-Tetrahydro-6-methyl-3-[2-(4-naphth-1-yl-3,4-dehydro-1-piperidinyl)ethyl]pyrrolo[3',4':4,5]thieno[2,3-d]-35 pyrimidin-4-one
33. 3,4,5,7-Tetrahydro-6-acetyl-3-[2-(4-(2-methoxyphenyl)-1-piperazinyl)ethyl]pyrrolo[3',4':4,5]thieno[2,3-d]pyrimidin-4-one
34. 3,4,5,7-Tetrahydro-6-acetyl-3-[2-(4-(2-methyl-1-naphthyl)-1-piperazinyl)ethyl]pyrrolo[3',4':4,5]thieno[2,3-d]pyrimidin-4-one 35. 3,4,5,7-Tetrahydro-6-benzyl-3-[2-(4-(2-methoxyphenyl)-1-piperazinyl)ethyl]pyrrolo[3',4':4,5]thieno[2,3-d]pyrimidin-4-one
36. 3,4,5,7-Tetrahydro-6-(4-nitrophenyl-2-ethyl)-3-[2-(4-(1-naphthyl)-1-piperazinyl)ethyl]pyrrolo[3',4':4,5]thieno[2,3-d]pyrimidin-4-one
37. 3,4,5,7-Tetrahydro-6-(4-aminobenzyl)-3-[2-(4-(2-methyl-1-naphthyl)-1-piperazinyl)ethyl]pyrrolo[3',4':4,5]thieno[2,3-d]pyrimidin-4-one
38. 3,4,5,7-Tetrahydro-6-carbethoxy-3-[2-(4-(2-methylphenyl)-1-piperazinyl)ethyl]pyrrolo[3',4':4,5]thieno[2,3-d]pyrimidin-4-one, melting point 152° C.
39. 3,4,5,7-Tetrahydro-6-carbethoxy-3-[2-(4-(2-chlorophenyl)-1-piperazinyl)ethyl]pyrrolo[3',4':4,5]thieno[2,3-d]pyrimidin-4-one, melting point 172° C.
40. 3,4,5,7-Tetrahydro-6-carbethoxy-3-[2-(4-(2-phenyl-1-piperidinyl)ethyl]pyrrolo[3',4':4,5]thieno[2,3-d]pyrimidin-4-one [sic]
41. 3,4,5,7-Tetrahydro-6-carbethoxy-3-[2-(4-(2-naphth-1-yl-1-piperidinyl)ethyl]pyrrolo[3',4':4,5]thieno[2,3-d]pyrimidin-4-one [sic]
42. 3,4,5,7-Tetrahydro-6-carbethoxy-3-[2-(4-(2-naphth-1-yl-3,4-dehydro-1-piperidinyl)ethyl]-pyrrolo[3',4':4,5]thieno[2,3-d]pyrimidin-4-one [sic]
43. 3,4,5,7-Tetrahydro-6-carbethoxy-3-[3-(4-(2-cyanophenyl)-1-piperazinyl)propyl]pyrrolo[3',4':4,5]thieno[2,3-d]pyrimidin-4-one, melting point 190° C.
44. 3,4,5,7-Tetrahydro-6-carbethoxy-3-[2-(4-(indan-4-yl-1-piperazinyl)ethyl]pyrrolo[3',4':4,5]thieno[2,3-d]pyrimidin-4-one, melting point 149° C.

We claim:
1. A 3,4,5,7-tetrahydropyrrolo[3',4':4,5]-thieno[2,3-d]pyrimidine compound of formula I

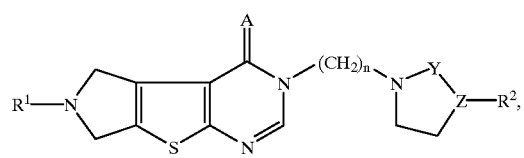

wherein
$R^1$ is a hydrogen atom, a $C_1$–$C_4$-alkyl group, an acetyl group, a $C_1$–$C_3$-alkyl carboxylate radical, or is a phenyl-$C_1$–$C_4$-alkyl radical where the aromatic ring is unsubstituted or substituted by halogen, $C_1$–$C_4$-alkyl, trifluoromethyl, hydroxyl, $C_1$–$C_4$-alkoxy, amino, cyano or nitro groups,
$R^2$ is a phenyl, pyridyl, pyrimidinyl or pyrazinyl group which is unsubstituted or mono- or disubstituted by halogen atoms, $C_1$–$C_4$-alkyl, trifluoromethyl, trifluoromethoxy, hydroxyl, $C_1$–$C_4$-alkoxy, amino, monomethylamino, dimethylamino, cyano or nitro groups, and may be fused to a benzene nucleus which may be mono- or disubstituted by halogen atoms, $C_1$–$C_4$-alkyl, hydroxyl, trifluoromethyl, $C_1$–$C_4$-alkoxy, amino, cyano or nitro groups and may contain 1 nitrogen atom, or to a 5- or 6-membered ring which may contain 1–2 oxygen atoms,
A is NH or an oxygen atom,
Y is $CH_2$, $CH_2$—$CH_2$, $CH_2$—$CH_2$—$CH_2$ or $CH_2$—CH,
Z is a nitrogen atom, carbon atom or CH, where the linkage between Y and Z may also be a double bond, and
n is 2, 3 or 4, or a physiologically tolerated salt thereof.

2. The compound defined in claim 1, wherein
$R^1$ is hydrogen, ethyl, ethoxycarbonyl
$R^2$ is o-methoxyphenyl, 1-naphthyl, 2-methoxy-1-naphthyl, 2-methyl-1-naphthyl
A is an oxygen atom
Y is $CH_2$—$CH_2$
Z is a nitrogen atom and
n is 2 and 3.

3. A pharmaceutical composition comprising an effective amount of the compound of formula I defined in claim 1 or a pysiologically tolerated salt thereof and at least one conventional excipient or diluent.

4. The composition defined in claim 3, which is adapted for the treatment of depression and related disorders.

5. A composition for the treatment of a pathological state in which the serotonin concentration is reduced, comprising at least one conventional excipient or diluent and the compound of formula I defined in claim 1 or a pysiologically tolerated salt thereof in an amount which is effective to selectively antagonize 5-$HT_{1B}$ and 5-$HT_{1A}$.

6. The composition defined in claim 5, wherein the amount is effective to supplement the selective antagonism by inhibiting serotonin reuptake.

7. A method of treating depression or a related disorder selected from the group consisting of mood disturbances with a central nervous causation, memory disturbances and psychogenic eating disorders, which method comprises administering effective amounts of the compound of formula (I) defined in claim 1 or a pysiologically tolerated salt thereof to a patient in need of such treatment.

8. The method of claim 7, wherein the patient is in a pathological state in which the serotonin concentration is reduced.

9. The method of claim 8, wherein the amount of the compound of formula (I) or the salt thereof is adapted to antagonize the serotonin receptors 5-$HT_{1B}$ and 5-$HT_{1A}$.

10. The method of claim 9, wherein the amount of the compound of formula (I) or the salt thereof is adapted to inhibit the serotonin reuptake.

11. A method of treating a pathological state in which the serotonin concentration is reduced in a patient, which pathological state is selected from the group of hyperprolactinemia, vasospasms, hypertension, gastrointestinal disorders associated with motility and secretion disturbances and sexual disorders, which method comprises administering effective amounts of the compound of formula (I) defined in claim 1 or a pysiologically tolerated salt thereof to a patient in need of such treatment.

12. The method of claim 11, wherein the amount of the compound of formula (I) or the salt thereof is adapted to antagonize the serotonin receptors 5-$HT_{1B}$ and 5-$HT_{1A}$.

13. The method of claim 12, wherein the amount of the compound of formula (I) or the salt thereof is adapted to inhibit the serotonin reuptake.

* * * * *